United States Patent [19]

Schrump et al.

[11] Patent Number: 5,173,292

[45] Date of Patent: Dec. 22, 1992

[54] MONOCLONAL ANTIBODIES WHICH SPECIFICALLY RECOGNIZE GALACTOSYL-GLOBOSIDE, COMPOSITIONS CONTAINING SAME AND METHODS OF USING SAME

[75] Inventors: David S. Schrump, Chicago, Ill.; Koichi Furukawa, New York, N.Y.; Hiroshi Yamaguchi, Nagoya, Japan; Kenneth O. Lloyd, Bronx; Lloyd J. Old, New York, both of N.Y.

[73] Assignee: Sloan-Kettering Institute for Cancer Research, New York, N.Y.

[21] Appl. No.: 212,312

[22] Filed: Jun. 14, 1988

[51] Int. Cl.$^5$ .................. A61K 37/66; C12H 5/00; C61K 35/14

[52] U.S. Cl. .................. 530/387.5; 435/240.27; 435/7.23; 530/388.15; 530/391.3; 530/388.8; 424/9; 424/85.8

[58] Field of Search .............. 530/389, 387; 424/85.8; 435/240.27

[56] References Cited

U.S. PATENT DOCUMENTS

| | | | |
|---|---|---|---|
| 4,334,017 | 6/1982 | Plotkin et al. | 435/7 |
| 4,507,391 | 3/1985 | Pukel et al. | 436/504 |
| 4,885,358 | 12/1989 | Kannagi et al. | 530/387 |
| 4,906,562 | 3/1990 | Hellstrom et al. | 435/7 |

OTHER PUBLICATIONS

Young, et al.; Journal of Biological Chemistry, vol. 256 (21), pp. 10967–10972 (1981).

Bremer et al., Journal of Biological Chemistry, vol. 259 (23) pp. 14773–14777 (1984).

Kannagi et al.; Journal of Biological Chemistry, vol. 258 (14) pp. 8934–8942 (1983).

Shevinsky et al.; Cell, vol. 30, pp. 697–706 (1982).

Primary Examiner—Frederick E. Waddell
Assistant Examiner—T. J. Criares
Attorney, Agent, or Firm—John P. White

[57] ABSTRACT

This invention provides a composition useful for diagnosing cancer which specifically recognizes a galactosyl-globoside. Preferably, the composition is a monoclonal antibody which specifically recognize the galactosyl-globoside antigen, gal-Gb4.

Additionally, the present invention provides two hybridoma cell lines, designated J309 and D579, which produce monoclonal antibodies that specifically recognize gal-Gb4.

The invention also provides a method of diagnosing a carcinoma which comprises contacting a sample from a human subject with a composition which specifically recognizes a galactosyl-globoside antigen and is labeled with a detectable moiety, under suitable conditions so as to form a detectable complex. The amount of formed complex is then quantified and correlated with values obtained from subjects devoid of carcinomas.

Another aspect of the invention provides a method of treating carcinoma which comprises administering an effective amount of galactosyl-globoside or an analog thereof and a pharmaceutically carrier to stimulate the body production of antibodies.

8 Claims, 4 Drawing Sheets

MONOCLONAL ANTIBODIES WHICH SPECIFICALLY RECOGNIZE GALACTOSYL-GLOBOSIDE, COMPOSITIONS CONTAINING SAME AND METHODS OF USING SAME

This invention described herein was made in the course of work under Grant Nos. CA-09149-12 and CA-47427 from the National Cancer Institute, National Institutes of Health, U.S. Department of Health and Human Services. The United States Government has certain rights in this invention.

BACKGROUND OF THE INVENTION

Throughout this application various publications are referenced by Arabic numerals. Full citations for these references may be found at the end of the specification immediately preceding the claims. The disclosures of these publications in their entireties are hereby incorporated by reference into this application in order to more fully describe the state of the art to which this invention pertains.

Techniques to analyze the humoral immune response at a clonal level have given new impetus to the search for human antibodies with cancer specificity. In the case of melanoma where analysis has progressed the furthest, human monoclonal antibodies (mAbs) have been islolated that show specificity for gangliosides such as GM3, GM2, GD3 or GD2 (1-3). Although these gangliosides are expressed on the surfaces of melanoma cells, they are also found in normal tissues, particularly tissues of neuroectodermal origin. For this reason it is not clear what role, if any, the tumor has in initiating ganglioside antibodies in melanoma patients, and whether such antibodies could be generated as frequently from the lymphocytes of normal individuals. In the case of epithelial cancers, human mAbs with cell surface reactivity have been isolated from patients with breast (4,5), colon (6,7) and lung (8) cancer. A mAb generated from lymphocytes of a patient with lung cancer showed specificity for the i antigen, a blood group precursor structure (8). The surface antigens recognized by antibodies from the other patients with epithelial cancers have not been structurally characterized.

The present invention provides monoclonal antibodies which specifically bind to galactosyl-globoside antigens found on the surface of epithelial cancer cells, particularly primary lung cancer. Additionally, the invention provides hybridomas produced by the fusion of a mouse myeloma cell line with lymph node lymphocytes from a patient with primary lung cancer.

SUMMARY OF THE INVENTION

This invention provides a composition useful for diagnosing cancer which specifically recognizes a galactosyl-globoside. Preferably, the composition is a monoclonal antibody which specifically recognize the galactosyl-globoside antigen, gal-Gb4.

Additionally, the present invention provides two hybridoma cell lines, designated J309 and D579, which have been deposited with the American Type Culture Collection (ATCC) under Accession Number HB 9748 and Accession Number HB 9749, respectively. The hybridoma cell lines, J309 and D579, were deposited pursuant to, and in satisfaction of the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. HB 9748 and HB 9749, respectively. Both hybridomas produce monoclonal antibodies which specifically recognize gal-Gb4.

The invention also provides a method of diagnosing a carcinoma which comprises contacting a sample from a human subject with a composition which specifically recognizes a galactosyl-globoside antigen and is labeled with a detectable moiety, under suitable conditions so as to form a detectable complex. The amount of formed complex is then quantified and correlated with values obtained from subjects devoid of carcinomas.

The invention further provides a method of in vivo carcinoma diagnosis which comprises administering to a human subject a suitable amount of a composition of the present invention labeled with a detectable moiety under suitable conditions so as to allow the composition to form a complex with the carcinoma surface antigen and detecting the complex so formed, thereby diagnosing cancer in the subject.

Another aspect of the invention provides a method of treating carcinoma which comprises administering an effective amount of galactosyl-globoside or an analog thereof and a pharmaceutically carrier to stimulate the body production of antibodies.

DETAILED DESCRIPTION OF THE INVENTION

Figure 1:
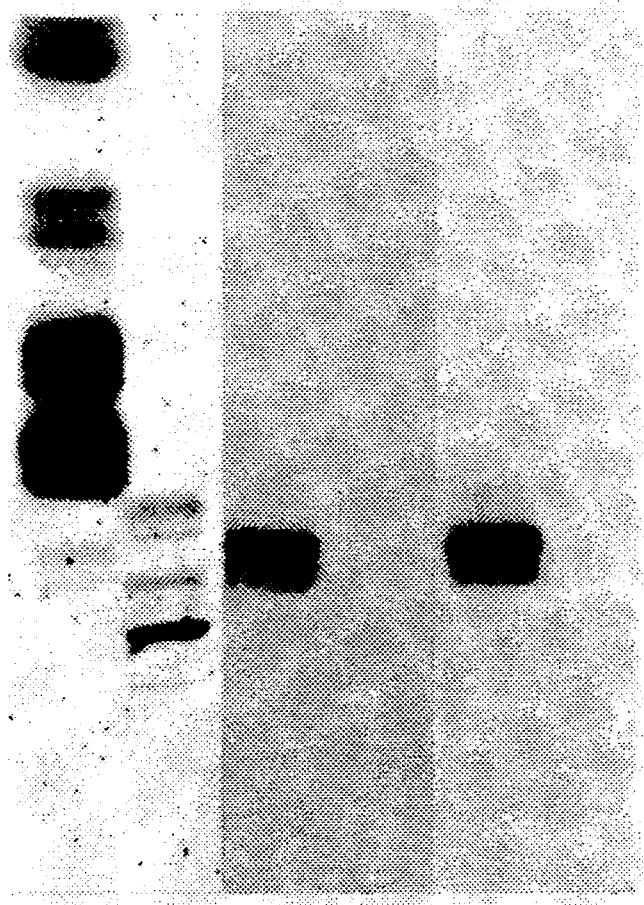
FIG. 1. Immunostaining of MCF-7 glycolipids with J309 and D579 antibodies. Orcinol (ORC) panel: HPTLC of MCF-7 neutral (N) and acidic (A) glycolipids (orcinal spray). J309 and D579 panels: neutral and acidic glycolipids immunostained with antibodies J309 and D579.

The invention provides a composition useful for diagnosing cancer which specifically recognizes a galactosyl-globoside or an analog thereof found on the surface of a cancer cell. The galactosyl-globoside which is recognized preferentially contains the sequence Galβ1-3GalNAcβ1-3Galα1-4Galβ1-4Glc and most preferably is gal-Gb4.

The invention also provides for two monoclonal antibodies which specifically recognize galactosyl-globoside antigens, particularly gal-Gb4. The monoclonal antibodies may be murine or human monoclonal antibodies.

Additionally, this invention provides two hybridoma cell lines designated J309 and D579. Both hybridomas have been deposited with the American Type Culture, Collection (ATCC) under Accession Number HB 9748 and Accession Number HB 9749, respectively. The hybridoma cell lines, J309 and D579, were deposited pursuant to, and in satisfaction of the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession No. HB 9748 and HB 9749, respectively. Both hybridoma cell lines produce human monoclonal antibodies which specifically recognize galactosylgloboside antigens, particularly gal-Gb4.

The monoclonal antibodies of this invention may be labeled with a detectable moiety. This moiety may comprise any one or more of the following: an enzyme, a radioactive label, a chromosphere, a fluorophore, an x-ray opaque material, a paramagnetic material and a chelated metal. This list is not inclusive, rather it is only to illustrate examples of detectable moieties.

This invention also provides a method of diagnosing a carcinoma. This method comprises contacting a sample from a human subject with the composition of the present invention which specifically recognizes the galactosyl-globoside antigen and is labeled with a detectable moiety, under suitable conditions so as to form a detectable complex. The amount of formed complex is then quantified and correlated with values obtained from subjects devoid of carcinomas. Merely by way of example, the sample from a human subject may comprise a tissue sample, sera, urine, cerebro-spinal fluid, ammiotic fluid, sputum, lung lavage, ascites fluid, saliva or any mucus type body secretion.

In the preferred embodiments, the invention provides a method in which primary lung cancer in a patient is diagnosed by quantitatively detecting gal-Gb4 in a sample of tissue cells or bodily fluid obtained from the patient and comparing the amount of gal-Gb4 with the amount present in a sample obtained from a subject without a carcinoma.

Another aspect of the invention also provides a method of in vivo carcinoma diagnosis. The method comprises administering to a human subject a suitable amount of the composition of the present invention labeled with a detectable moiety under suitable conditions so as to allow the composition to form a complex with a carcinoma surface antigen and detecting the complex so formed, thereby diagnosing carcinoma in the subject. Preferably, the carcinoma surface antigen comprises the sequence Gal$\beta$1-3GalNAc$\beta$1-3Gal$\alpha$1-4Gal$\beta$1-4Glc.

This invention further provides a conjugate comprising monoclonal antibodies of this invention attached to a cytotoxic tumor agent and a therapeutic composition comprising an effective carcinoma growth inhibiting amount of this conjugate and a pharmaceutically acceptable carrier. The growth inhibiting amount may be an amount sufficient to kill the carcinoma. Merely by way of example, suitable pharmaceutically acceptable carriers may include water, buffered saline or glucose solutions.

This invention still further provides a method of treating carcinoma in a human subject which comprises administering to the subject an effective therapeutic amount of the composition of monoclonal antibody-cytotoxic tumor agent complex.

Additionally, the invention provides a method of treating carcinoma which comprises administering an effective amount of galactosyl-globoside or an analog thereof and a pharmaceutically acceptable carrier to stimulate the body's production of antibodies. Merely by way of example suitable analogs may be structured analogs or anti-idiotype antibodies.

The present invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Lymph node lymphocytes from patients with primary lung cancer were immortalized with Epstein-Barr virus and culture supernatants were screened for cell surface reactivity against allogeneic cancer cell lines. The percentage of wells containing detectable antibodies in initial screening ranged from 0-17%, but the vast majority of the cultures lost antibody activity on subsequent expansion. Two antibody-secreting clones, J309 and D579, derived from separate individuals and reactive with anaplastic lung cancer cell lines, were successfully expanded and fused with the NS-1 mouse myeloma cell line. The antibodies produced by these clones exhibited identical restricted serologic reactivity against culture cell lines and detected a carbohydrate antigen present in the neutral glycolipid fraction of MCF-7 breast cancer cells. Serologic, immunochemical and chemical analyses revealed that the antigen recognized by antibodies J309 and D579 is galactosyl-globoside (Gal$\beta$1-3 GalNAc$\beta$1-3 Gal$\alpha$1-4 Gal$\beta$1-4-Glc-Cer).

MATERIALS AND METHODS

Tissue culture. Small cell lung cancer lines NCI-H69 and NCI-H129 were obtained from American Tissue Culture Collection (ATCC, Bethesda, Md.). All other cell lines were obtained from our cell bank. Cell lines were passaged as described previously (9).

Generation of human mAbs. Lymph node lymphocytes isolated by Ficoll-Hypaque were immortalized with EBV (ref. 3). Cells were plated in RPMI 1640 medium containing 10% FCS at a concentration of $5\times10^3 - 1\times10^4$ cells/well in 96-well tissue plates. Wells containing cell surface-reactive clones were expanded, subcultured by limiting dilution, and fused with the NS-1 mouse myeloma cell line as described (3,4).

Serologic assays. Immune adherence (IA) and enzymelinked immunoadsorbent (ELISA) assays were performed as described (10,11).

Antibodies. Mouse mAbs 1B-2 recognizing paragloboside (LNneoT) (12), and H-11, recognizing H-type 2 structure (13) were provided by S. Hakomori (University of Washington, Seattle, Wash.), and R. Knowles (Sloan-Kettering Institute, New York, N.Y.), respectively. Rat mAb SSEA-3 (ref. 14), which recognizes gal-Gb4 preferentially but which is also reactive with Gb4 and, globo-H structures (15), was provided by D. Solter (Wistar Institute, Philadelphia, Pa.). Mouse mAb MBr1 (ref. 16), which recognizes globo-H structure preferentially but which is also reactive with gal-Gb4 (ref. 17), was provided by M. Colnaghi (Istituto Nazionale, Milan, Italy).

Glycolipids. Isolation of neutral and acidic glycolipids was performed as described previously (18). MCF-7 neutral glycolipids were purified by HPLC and preparative TLC techniques. HPLC was performed with a Varian 5000 apparatus (Varian Associates, Inc., Walnut Creek, Calif.) equipped with a silica column (0.45×25 cm) (Supelco, Inc., Bellefonte, Pa.) using an isopropanol:hexane:water solvent elution gradient of 55:43:2 to 55:39:6. Preparative TLC was performed using silica G plates (Fisher Scientific) and a solvent system of chloroform:mthanol:water 60:35:8 (ref. 19); HPLC and TLC for immunostaining were performed using this solvent system as well. Immunostaining after TLC was performed as described with modifications (20,21). Antiobdy dilutions for immunostaining experiments were as follows: J309 and D579: 1:5 dilution of hybridoma supernatant; SSEA-3 and MBR1: 1:1000 dilution of ascites fluid.

Immunochemical analysis: $\beta$—Galactosidase treatment. MCF-7 neutral glycolipids were treated with $\beta$-galactosidase (C. lampus, Miles Scientific) using a modification of the technique reported by Kannagi et al. (15). Briefly, 0.3 $\mu$g of MCF-7 neutral glycolipid were reacted with 0.06 units of $\beta$-galactosidase in 100 mM sodium citrate buffer (ph 4.0) containing 1 mg/ml sodium taurodesoxycholate (Sigma). $\beta$-Galactosidase activity was verified by the ability of this enzyme to degrade a paraglobside standard, resulting in the loss of immunostaining of this structure by antibody 1B-2. Control (untreated) samples received buffer without enzyme. Following incubation at 37° C. for 18 hrs, reactions were terminated and glycolipid samples were prepared similarly to those in the fucosidase treatment experiments.

$\alpha$-L-fuscosidase treatment. Approximately 0.3 $\mu$g of MCF-7 neutral glycolipids were reacted with 0.3 units of $\alpha$-L-fuscosidase (Behringer-Mannheim) as described (22). Fucosidase activity was verified by the ability of this enzym to degrade the h-type 2 structure from human ORBC, resulting in the loss of immunostaining of this determinant by antibody H-11. Control (untreated) samples received buffer without enzyme.

Gas-liquid chromatography analysis of sugar components. After methanolysis and trifluoracetylation (23), sugar components in the purified glycolipids were analyzed using a Perkin-Elmer gas chromatograph Model 8400 and 5% SP-2401 on 100/200 Supelcoport column (Supelco).

Methylation analysis of MCF-7 neutral glycolipid. MCF-7 fraction 2b was methylated according to ref. 24.; after hydrolysis in $H_2SO_4$—$CH_3COOH$ (25), individual methylated sugars were identified as their O-acetylated hexitol derivatives as described by Bjorndal et al. (26). GC/MS was carried out on a VG 70-250 double magnetic focusing deflection instrument coupled to a HP 5790A gas chromatograph at the Rockefeller University Mass Spectrometric Biotechnology Research Resource.

Results Over 7300 wells containing EBV-transformed lymphocytes derived from regional lymph nodes of nine patients with primary lung cancer were screened for cell surface reactivity against allogeneic cancer lines using an immune adherence (IA) assay. Initial screening panels were tailored to include target cells with defined blood group phenotypes originating from lung cancers of various histological types. The percentage of wells containing cell surface-reaction antibodies varied from patient to patient, ranging from 0–17%. A total of 460 wells (6%) contained cell surface reactive antibodies in initial screening. Only five of these showed continued antibody secretion during culture expansion. Two of these expanded cultures were fused with NS-1 and resulted in the J309 and D579 clones, both of which secrete IgM antibodies. J309 was derived from one of 65 cell surface-reactive cultures identified during the initial screening of 825 wells containing EBV-immortalized lymphocytes obtained from nodes adjacent to a highly anaplastic lung cancer (Table 1). A variety of cell surface reactivities were observed, with the most frequent pattern (29 wells) involving reactivity with Calu-6, SK-LU-1 and MCF-7 cell lines; J309 was isolated from an expand culture having this reactivity pattern. D579 was derived from one of 91 cell surface-reactive cultures identified during the screening of 960 wells containing EBV-immortalized lymphocytes originating from nodes adjacent to a high-grade epidermoid lung cancer. D579 isolated from one of 33 wells containing antibody reactive with Calu-6. (SK-LU-1 and MCF-7 cell lines were not included in this screening panel.)

TABLE 1

CELL SURFACE REACTIVITY (IA ASSAY) OF SUPERNATANTS FROM EBV-TRANSFORMED LYMPHOCYTES OBTAINED FROM LYMPH NODES ADJACENT TO A PRIMARY ANAPLASTIC LUNG CANCER

| Calu-6* | SK-LU-1* | SK-LC-9** | SK-LC-25** | MCF-7 | NUMBER OF WELLS |
|---|---|---|---|---|---|
| + | | | | | 4 |
| | + | | | | 1 |
| | | + | | | 8 |
| | | | + | | 2 |
| | | | | + | 7 |
| + | + | | | | 3 |
| + | | | | + | 5 |
| | | + | | + | 1 |
| | | | + | + | 1 |
| + | + | + | | | 1 |
| + | + | | | + | 29 |
| + | | + | | + | 1 |
| + | + | + | | + | 2 |

*Calu-6, SK-LU-1: derived from anaplastic lung cancers
**SK-LC-9, SK-LC-25: derived from lung adenocarcinomas
MCF-7: derived from breast cancer effusion Table 2 summarizes the reactivity patterns of anitibodies J309 and D579 against an extended cell panel. These antibodies showed identical reactions that were restricted to anaplastic lung cancer lines (Calu-6, SK-LU-1, SK-LC-21), 2/10 breast cancer lines (MCF-7, 734-B), and ⅓ teratocarcinoma lines (833-K). No reactivity was noted with over 70 cell lines derived from either normal or malignant cells of endodermal, ectodermal, neuroectodermal or mesodermal origin. Moderate reactivity was observed against short-term cultures of normal kidney epithelium. No reactivity was noted with human or sheep erythrocytes, or EBV-transformed lymphocytes.

Figure 2:
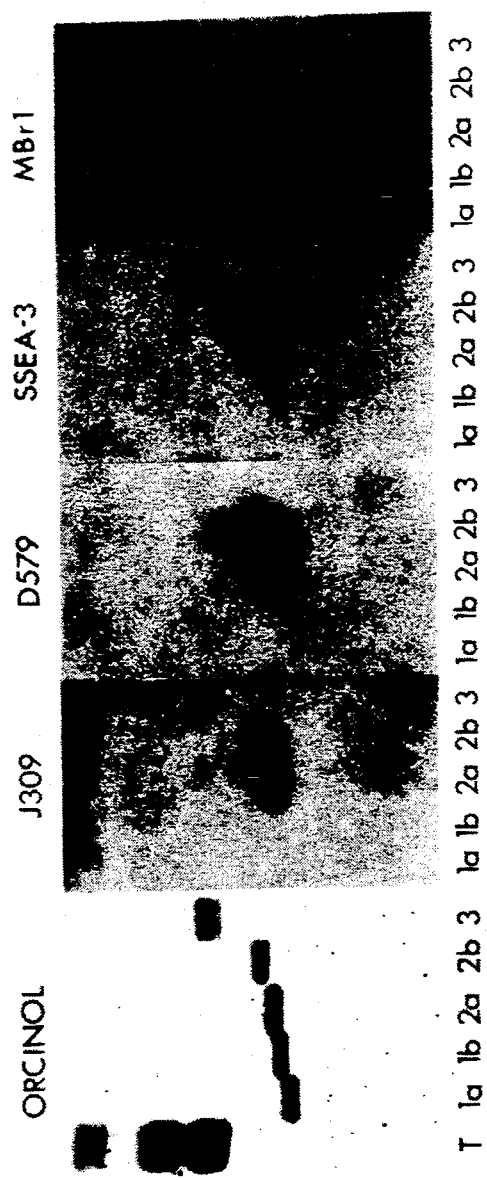
FIG. 2. Immunostaining of purified MCF-7 neutral glycolipids with J309, D579, SSEA-3 and MBr1 antibodies. Orcinol panel: HPTLC of total MCF-7 neutral glycolipids (T) and purified glycolipid fractions 1a, 1b, 2a, 2b and 3 (orcinol spray). J309, D579, SSEA-3, and MBr1 panels: purified neutral glycolipid fractions immunostained with antibodies J309, D579, SSEA-3 and MBr1.

1b, and to a lesser degree with fractions 2a and 2b (FIG. 2).

TABLE 2

SEROLOGIC REACTIVITY OF J309, D579, SSEA-3 AND MBr1 ANTIBODIES AGAINST CULTURED CELL LINES (IMMUNE ADHERENCE ASSAY)

| CELL TYPES | J309 | D579 | SSEA-3 | MRr1 |
|---|---|---|---|---|
| LUNG: SK-LC-1,-2,-6,-8,-9,-10,-12,-13,-14,-15 | 0000000000 | 0000000000 | 0000000 00 | 0000000 00 |
| -17,-20,-21,-25,SK-LU-1,Calu-1,-6,SK-Mes-1,NCI-H69,-H129 | 00 0 0 000 | 00 0 0 000 | 00 0 0 0 | 0000 0 0 |
| BREAST: SK-Br-5,-7,BT-20,CAMA,734-B,MDA-MB-157,-231,-361,AlAb,MCF-7 | 0000 0000 | 0000 0000 | 0000 0000 | 0000 0000 |
| GASTRIC/PANCREATIC: NUGC-3,NUGC-4,ASPC-1 | 000 | 000 | 000 | 000 |
| COLON: SK-CO-1,-10,DLD-1,HT-20,SW-480,-620,-1083,-1116,-1417,HCT-116 | 0000000000 | 0000000000 | 0000000000 | 0000000000 |
| RENAL: SK-RC-2,-6,-7,-9,-17,-18,-29,-39,-49,-52 | 0000000000 | 0000000000 | 0 000 0 | 0000000000 |
| BLADDER: T-24,RT-4,S-637,639-V | 0000 | 0000 | 0000 | 0 |
| OVARIAN/UTERINE: SK-OV-3,-4,-6,2774,SW-626,SK-UT-1 | 000000 | 000000 | 00 00 | 00 00 |
| TERATOCARCINOMA: Tera-1,Tera-2,833-K | 00 | 00 | 00 | 00 |
| MELANOMA: SK-MEL-13,-23,-28,-31,-37,-61,-94,-130,-173,MeWo | 0000000000 | 0000000000 | 0000000000 | 0000000000 |
| ASTROCYTOMA/NEUROBLASTOMA: SK-MG-4,-6,IMR-32,U25-MG | 0000 | 0000 | 0000 | 0000 |
| LEUKEMIA/LYMPHOMA: CCRF-CEM,-HSB-2,P12,SK-LY-16,BALL-1, Daudi,NALM-1,HL-60,K562,KG1 | 0000000000 | 0000000000 | 000 000000 | 0 0000000 |
| EBV-TRANSFORMED LYMPHOCYTES | 00000 | 00000 | N.T. | N.T. |
| FIBROBLASTS: WI-38,F-135-60-86 | 00 | 00 | N.T. | N.T. |
| NORMAL KIDNEY | 0 | 0 | N.T. | N.T. |
| HUMAN A,B,O ERYTHROCYTES (HEMAGGLUTINATION ASSAY) | 000 | 000 | N.T. | N.T. |
| SHEEP ERYTHROCYTES (HEMAGGLUTINATION ASSAY) | 0 | 0 | N.T. | N.T. |

0, no reactivity; 0. reactivity with J309 or D579 (hybridoma supernatants) and SSEA-3 or MBr1 (ascites fluid). Titers with human mAbs: $10^{-2} - 10^{-3}$; titers with rodent mAbs: $10^{-3} > 10^{-5}$. N.T., not tested.

formed lymphocytes.

Initial analysis revealed that J309 and D579 recognized heat-stable antigens presented in the neutral glycolipid fraction of MCF-7 cells (FIG. 1). Immunostaining of MCF-7 neutral glycolipids purified by HPLC and preparative TLC demonstrated that J309 and D579 reacted with fractions 2a and 2b (FIG. 2), a finding consistent with serologic data suggesting that these two antibodies recognized the same antigen.

The specificity of antibodies J309 and D579 was shown to be unrelated to A, B, H, Le$^a$, Le$^b$, Le$^x$, Le$^y$ or type 1 and type 2 precursor structures as determined by analysis of cultured cell lines and glycoprotein preparations containing these lacto- or neolacto-series determinants. To investigate the possibility that J309 and D579 recognize extended globoseries determinants, the human antibodies were compared to two rodent antibodies (SSEA-3 and MBr1) that react with globoseries structures. The rodent antibodies exhibited restricted reactivity against the cultured cell panel (Table 2) and reacted the same lines recognized by J309 and D579 antibodies. A number of cell lines that did not react with the human antibodies showed reactivity with the rodent antibodies, but the structural basis for these individual discrepancies has not been defined Immunostaining of MCF-7 neutral glycolipids with SSEA-3 and MBr1 antibodies revealed the SSEA-3 reacted primarily with fractions 2a and 2b, and to a lesser extent with fraction 3, whereas MBr1 reacted strongly with fractions 1a and 1b, and to a lesser degree with fractions 2a and 2b (FIG. 2).

MCF-7 fraction 3 was identified as globoside (Gb4) on the basis of TLC migration similar to that of globoside from ORBC, reactivity with SSEA-3 antibody, and sugar analysis by gas chromatography (glc) (Table 3). Immunostaining data and glc analysis of the sugar content of fractions 2a and 2b suggested that both of these components represented gal-Gb4 (Table 3).

TABLE 3

CARBOHYDRATE COMPOSITION OF MCF-7 NEUTRAL GLYCOLIPIDS

| MCF-7 Fraction | Fucose | Galactose | Glucose | GalNAc | GlcNAc | Sialic Acid |
|---|---|---|---|---|---|---|
| 3 | 0 | 1.76 | 0.94 | 1.00 | 0 | 0 |
| 2b | 0 | 2.93 | 1.17 | 1.00 | 0 | 0 |
| 2a | 0.06 | 2.35 | 1.16 | 1.00 | 0.11 | 0.09 |

Figure 3:
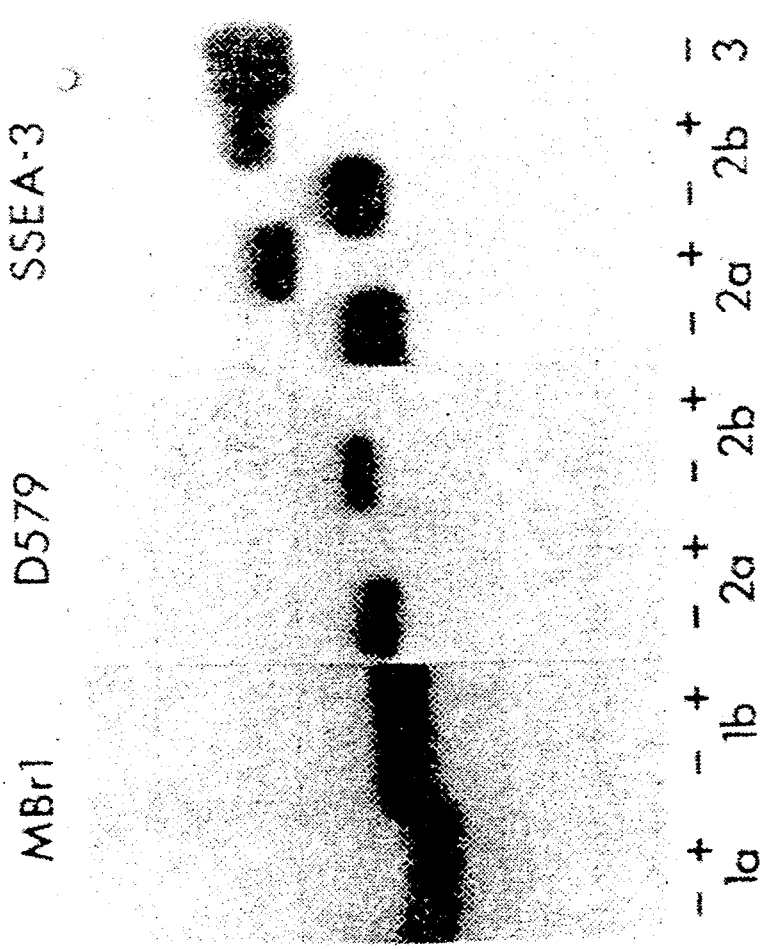
FIG. 3. β-Galactosidase treatment of purified MCF-7 neutral glycolipids. MBr1 panel: fractions 1a and 1b immunostained with antibody MBr1. D579 panel: fractions 2a and 2b immunostained with antibody D579. SSEA-3 panel: fractions 2a, 2b, and 3 immunostained with antibody SSEA-3. − = control sample, + = enzyme-treated sample.
Figure 4:
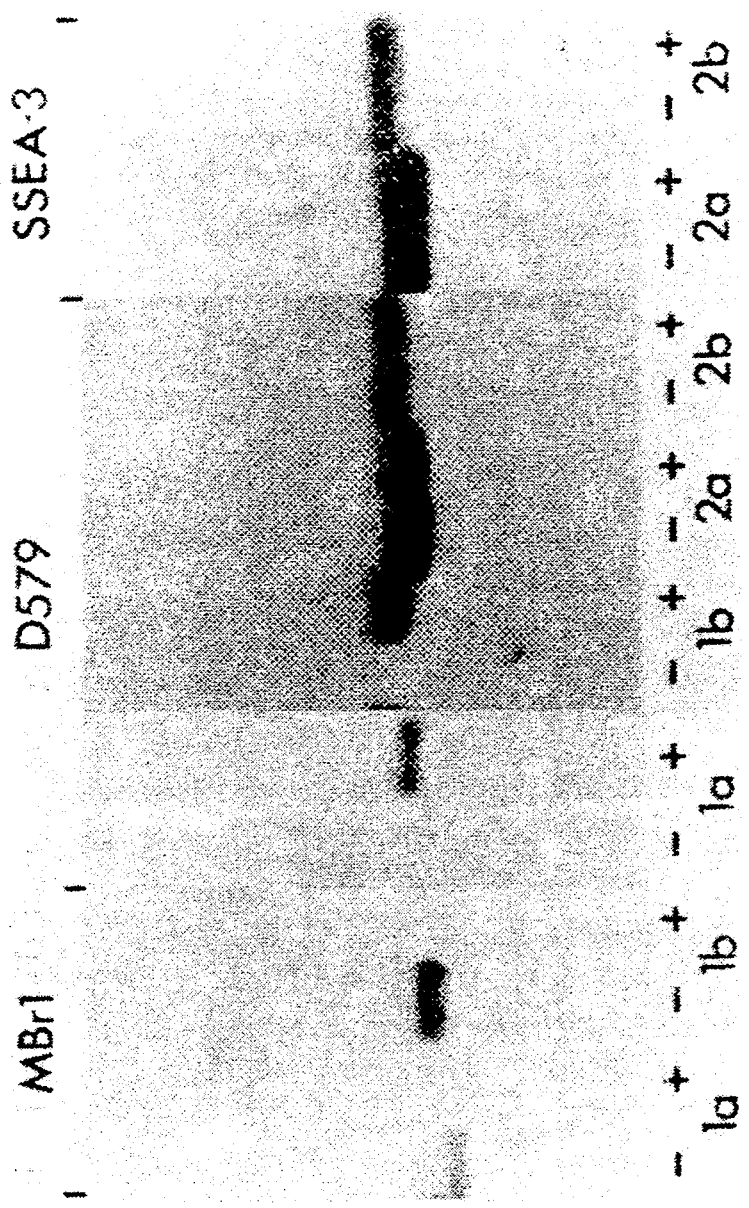
FIG. 4. α-L-Fucosidase treatment of purified MCF-7 neutral glycolipids. MBr1 panel: fractions 1a and 1b immunostained with antibody MBr1. D579 panel: fractions 1a, 1b, 2a and 2b immunostained with antibody D579. SSEA-3 panel: fractions 2a and 2b immunostained with antibody SSEA-3. − = control sample, + = enzyme-treated sample.

Exoglycosidase analysis of MCF-7 fractions 2a and 2b was undertaken to further verify the nature of these components. As shown in FIG. 3, $\beta$-galactosidase treatment of fractions 1a and 1b produced no degradation as evidenced by immunostaining with MBr1 antibody. In contrast, enzymatic treatment of fractions 2a and 2b abolished immunostaining of these components with D579 antibody, and generated products corresponding to lower and upper components of Gb4, respectively, which were detected by SSEA-3 antibody. On the other hand, treatment of fractions 1a and 1b with α-L-fucosidase converted these fractions to 2a and 2b, respectively, as evidenced by the simultaneous loss of immunostaining by MBr1 and detection by D579 of the conversion products; no significant effect was observed following fucosidase treatment of fractions 2a and 2b as determined by immunostaining with D579 and SSEA-3 antibodies (FIG. 4).

Methylation analysis of fraction 2b and identification of the resulting methylated sugar alcohols as their acetylated derivatives by GC/MS showed the presence of 2,3,4,6 tetra-O-methyl-1,5-di-O-acetyl-galactitol, 2,3,6,-tri-O-methyl-1,4,5-tri-O-acetyl-galactitol, 2,3,6-tri-O-methyl-1,4,5-tri-O-acetyl glucitol, 2,4,6-tri-O-methyl-2-acetamido-2-N-methyl-1,3,5-tri-O-acetyl-galactitol, and 4,6,di-O-methyl-2-acetamido-2-N-methyl-1,3,5-tri-O-acetyl-galactitol in approximately equimolar proportions. These derivatives revealed that the structure of fraction 2b contained a terminal galactose, a 4-linked galactose, a 4-linked glucose, a 3-linked galactose, and a 3-substituted N-acetyl-galactosamine such as would be found in a Gal $\beta$1-3 GalNAc $\beta$1-3Gal$\alpha$1-4Gal $\beta$1-4Glc Sequence.

These data are consistent with the interpretation that with different TLC migration rates, whereas fractions 1a and 1b represented two forms of the globo-H antigen. (Differing TLC migrations of components bearing identical carbohydrate determinants generally are attributed to differences in ceramide structures.) These findings are in accordance with previously published data concerning gal-Gb4 and globo-H determinants in 2102Ep teratocarcinoma and MCF-7 breast cancer cell lines (15,17).

Discussion

A major limitation in the use of EBV transformation to investigate immune recognition of tumor antigens in cancer patients continues to be the rapid loss of antibody-producing clones during culture expansion. Nevertheless, a low frequency of stable cultures can be isolated which provide enough supernatant for detailed serologic analysis and sufficient cells to generate NS-1 hybrids. In this study, two stable antibody secreting hybrids were isolated from two different individuals; antibody produced by an unstable NS-1 hybrid of EBV-transformed lymphocytes from another patient with lung cancer showed a gal-Gb4 reactivity pattern, and suggestive evidence for gal-Gb4 reactivity has also been observed during the initial screening of EBV-transformed lymphocytes from other lung cancer patients. J309 and D579 do not react with a variety of other globo-, lacto-, or ganglio-series carbohydrate structures, including Forssman antigen (GalNAc $\alpha$1-3Gb4) and asialo GM1 (Gal $\beta$1-3GalNAc$\beta$1-4Gal$\beta$1-4-Glc), or asialoglycophorin preparations containing T blood group determinants (27).

J309 and D579 were compared to two rodent mAbs (SSEA-3 and MBr1) recognizing extended globo-series determinants. The human and rodent mAbs showed remarkably similar and restricted reactivity patterns on cultured cell lines despite the broader reactivity of the rodent mAbs with isolated glycolipids. Extended globo-series antigens thus appear to have a more restricted distribution on the surface of cultured cancer cell lines than lacto-series antigens, which are commonly detected on cultured epithelial cancers (28).

Limited information is available concerning the distribution of extended globo-series structures in normal and neoplastic tissues, and the frequency of naturally occurring antibodies to these structures in normal and tumor-bearing individuals. MBr1 reactivity has been detected in normal and malignant breast epithelium, lung cancers, and normal and neoplastic epithelial tissues in the genito-urinary system (29). Galactosyl-globoside and sialylated gal-Gb4 have been identified on human embryonal carcinoma cells (15,30,31), but their distribution in other human tissues has not been analyzed. Although generally thought to be absent in humans, Forssman antigen has been reported to be present in normal and neoplastic tissues of the gastrointestinal tract (32). Naturally occurring serum antibodies reactive with Forssman antigen are present in normal individuals, and have been observed to be decreased in patients with gastric cancer (33). Information concerning naturally occurring antibodies to other extended globo-series structures is unavailable.

The fact that the lung cancer cell lines (Calu-6, SK-LU-1, SK-LC-21) expressing gal-Gb4 were derived from anaplastic tumors may be of significance. A shift from globo- to lacto-series glycolipid synthesis occurs during murine embryonic development (34,35) and chemically induced differentiation of human embryonal carcinoma cells (36,37). Such a globo- to lacto-series shift may also occur during differentiation of the pulmonary stem cell. Malignant transformation of early precursor cells may result in anaplastic tumors having a globo-phenotype, whereas transformation of more differentiated cells (or stem cells retaining the capacity to differentiate after transformation) may result in adeno- and squamous cell carcinomas having a predominantly lacto-series phenotype.

References

1. Cahan, L. D., Irie, R. F., Singh, R., Cassidenti, A., Paulson, J. C. (1982) Proc. Natl. Acad. Sci., U.S.A. 79:7629–7633.

2. Tai, T., Paulson, J. C., Cahan, L. D., Irie, R. F. (1983) Proc. Natl. Acad. Sci., U.S.A. 80:5392–5396.

3. Yamaguchi, H., Furukawa, K., Fortunato, S. R., Livingston, P. O., Lloyd, K. O, Oettgen, H. F., Old, L. J. (1987) Proc. Natl. Acad. Sci., U.S.A. 84:2416–2420.

4. Cote, R. J., Morrissey, D. M., Houghton, A. N., Beattie, E. J., Jr., Oettgen, H. F., Old, L. J. (1983). Proc. Natl. Acad. Sci., U.S.A. 80:2026–2030.

5. Cote, R. J., Morrissey, D. M., Houghton, A. N., Thomson, T. M., Daly, M. E., Oettgen, H. F., Old, L. J. (1986) Proc. Natl. Acad. Sci., U.S.A. 83:2959–2963.

6. Strelkauskas, A. J., Taylor, C. L., Aldenderfer, P. H., Warner, G. A. (1987) Immunology Series, Vol. 30, Human Hybridomas: Diagnostic and Therapeutic Applications, Strelkauskas, A. J., ed. (Marcel Dekker, Inc , N.Y.) pp. 227–251.

7. Haspel, M. V., McCabe, R. P., Pomato, N., Janesch, N. J., Knowlton, J. V., Peters, L. C., Hoover, H. C., Jr., Hanna, M. G., Jr. (1985) Cancer Res. 45:3951–3961.

8. Hirobashi, S., Clausen, H., Nudelman, E., Inoue, H., Shimosato, Y., Hakomori, S. (1986) J. Immunol. 136:4163–4168.

9. Carey, T. E., Takahashi, T., Resnick, L. A., Oettgen, H. F., Old, L. J. (1976) Proc. Natl. Acad. Sci., U.S.A. 73:3278–3282.

10. Shiku, H., Takahashi, T., Oettgen, H. F., Old. L. J. (1976) J. Exp. Med. 144:873–881.

11. Sakamoto, J., Yin, B. W. T., Lloyd, K. O. (1984) Mol. Immunol. 21:1093–1098.

12. Young, W. W., Jr., Portoukalian, J., Hakomori, S. (1981) J.Biol. Chem. 256:10967–10972.

13. Knowles, R. W., Bai, Y., Daniels, G. L., Watkins, W. (1982) J. Immunogenet. 9:69–76.

14. Shevinsky, L. H., Knowles, B. B., Damjanov, I., Solter, D. (1982) Cell 30:697–705.

15. Kannagi, R., Levery, D. S., Ishigami, F., Hakomori, S., Shevinsky, L. H., Knowles, B. B., Solter, D. (1983) J. Biol. Chem. 258:8934–8942.

16. Menard, S., Tagliabue, E., Canevari, S., Fossati, G., Colgnahi, M. I. (1983) Cancer Res. 43:1295–1300.

17. Bremer, E. C., Levery, S. B., Sonnino, S., Ghidoni, R., Canevari, S., Kannagi, R., Hakomori, S. (1984) J. Biol. Chem. 259:14773–14777.

18. Pukel, C. S., Lloyd, K. O., Travassos, L. R., Dippold, W. G., Oettgen, H. F., Old, L. J. (1982) J. Exp. Med. 155:1133–1147.

19.-Hakomori, S. (1983) Handbook of Lipid Research 3 -Sphingolipid Biochemistry, Kanfer, J., Hakomori, S., eds. (Plenum Press, New York), pp. 31-32.

20. Magnani, J. L., Smith, D. F., Ginsburg, V. (1980) Anal. Biochem. 109:399-402.

21. Furukawa, K., Clausen, H., Hakomori, S., Sakamoto, J., Look, K., Lundblad, A., Mattes, M. J., Lloyd, K. O. (1985) Biochem. 24:7820-7826.

22. Schwarting, G. A., Caroll, P. G., DeWolf, W. C. (1983) Biochem. Biophys. Res. Commun. 112:935-940.

23. Zanneta, J. P., Breckenridge, W. C., Vincendon, G. (1972) J. Chromatogr. 69:291-304.

24. Hakomori, S. (1964) J. Biochem. 55:205-208.

25. Yang, H-J., Hakomori, S. (1971) J. Biol. Chem. 246:1192-1200.

26. Bjorndal, H., Lindberg, B., Svensson, S. (1970) Carb. Res. 15:339-349.

27. Springer, G. F. (1984) Science 224:1198-1206.

28. Sakamoto, J., Furukawa, K., Cordon-Cardo, C., Yin, B. W. T., Rettig, W. J., Oettgen, H. F., Old, L. J., Lloyd, K. O. (1986) Cancer Res. 46:1553-1561.

29. Mariani-Costantini, R., Colnaghi, M. I., Leoni, F., Menard, S., Cerasoli, S., Rilke, F. (1984) Virchows Arch. Pathol. Anat. 402:389-404.

30. Kannagi, R., Cochran, N. A., Ishigami, F., Hakomori, S., Andrews, P. W., Knowles, B. B., Solter, D. (1983) EMBO J. 2:2355-2361.

31. Damjanov, I., Fox, N., Knowles, B. B., Solter, D., Lange, P. H., Fraley, E. E. (1982) Am. J. Pathol. 8:225-230.

32. Hakomori, S., Wang, S. M., Young, W. W., Jr. (1977) Proc. Natl. Acad. Sci., U.S.A. 74:3023-3027.

33. Young, W. W., Jr., Hakomori, S., Levine, P. (1979) J. Immunol. 123:92-96.

34. Hakomori, S., Kannagi, R. (1983) J. Natl. Cancer Inst. 71:231-251.

35. Stern, P. L. (1984) Brit. Med. Bull. 40:218-223.

36. Andrews, P. W., Goodfellow, P. N., Shevinsky, L. H., Bronson, D. L., Knowles, B. B. (1982) Int. J. Cancer 29:523-531.

37. Fenderson, B. A., Andrews, P. W. Nudelman, E., Clausen, H., Hakomori, S. (1987) Dev. Biol. 122:21-34.

What is claimed is:

1. A human monoclonal antibody which specifically recognizes a galactosyl-globoside found on the surface of a human cancer cell, which galactosyl-globoside is specifically recognized by a monoclonal antibody produced by a hybridoma cell line (ATTC Accession No. HB 9748) or a hybridoma cell line (ATTC Accession No. HB 9749).

2. A monoclonal antibody of claim 1, wherein the galactosyl-globoside comprises Gal$\beta$1-3GalNAc$\beta$1-3Gal$\alpha$1-4Gal$\beta$1-4Glc sequence.

3. A monoclonal antibody of claim 1, wherein the galactosyl-globoside is gal-Gb4.

4. A monoclonal antibody of claim 1 labeled with a detectable moiety.

5. A monoclonal antibody of claim 1 produced by a hybridoma cell line (ATCC Accession No. HB 9748.

6. A monoclonal antibody of claim 1 produced by a hybridoma cell line (ATCC Accession No. HB 9749).

7. A hybridoma cell line (ATCC Accession No. HB 9748).

8. A hybridoma cell line (ATCC Accession No. HB 9749).

* * * * *

UNITED STATES PATENT AND TRADEMARK OFFICE
CERTIFICATE OF CORRECTION

PATENT NO. : 5,173,292

DATED : December 22, 1992

INVENTOR(S) : David S. Schrump, et al.

It is certified that error appears in the above-identified patent and that said Letters Patent is hereby corrected as shown below:

In column 5, line 43; "enzym" should read --enzyme--.

In column 7, line 64; "defined Immunostaining" should read --defined. Immunostaining--.

In column 8, line 63; "methyl-1,4,5-tri-O-acetyl glucitol," should read --methyl-1,4,5-tri-O-acetyl-glucitol,--.

In column 9, line 5; after "interpretation that" please insert --fractions 2a and 2b represented the gal-Gb4 antigen--.

Signed and Sealed this

Fourteenth Day of December, 1993

*Attest:*

BRUCE LEHMAN

*Attesting Officer*   *Commissioner of Patents and Trademarks*